United States Patent [19]

DeMarinis

[11] 4,272,531
[45] Jun. 9, 1981

[54] 3,3'-BIS-METHYLENE-1,3-BENZO-THIAZINE COMPOUNDS

[75] Inventor: Robert M. DeMarinis, Ardmore, Pa.

[73] Assignee: SmithKline Corporation, Philadelphia, Pa.

[21] Appl. No.: 163,123

[22] Filed: Jun. 26, 1980

[51] Int. Cl.³ .................. C07D 417/06; A61K 31/54
[52] U.S. Cl. ...................................... 424/246; 544/50
[58] Field of Search .......................... 544/50; 424/246

[56] References Cited

U.S. PATENT DOCUMENTS 3,455,915  7/1969  Krapcho ................................ 544/50
3,475,423  10/1969  Krapcho ................................ 544/50

Primary Examiner—John M. Ford
Attorney, Agent, or Firm—Joseph A. Marlino; Richard D. Foggio; Alan D. Lourie

[57] ABSTRACT

3,3'-Bis-Methylene-1,3-benzothiazine compounds are inhibitors of phenylethanolamine N-methyl-transferase.

12 Claims, No Drawings

3,3'-BIS-METHYLENE-1,3-BENZO-THIAZINE COMPOUNDS

This invention relates to new 3,3'-bis-methylene-1,3-benzothiazine compounds. These compounds have pharmacological activity, in particular they inhibit the enzyme phenylethanolamine N-methyltransferase.

Epinephrine is a hormone, synthesized in the adrenal medulla, which is released into the blood stream in response to stress and produces profound physiological changes which serve to prepare the animal to cope with the stressor situation. For example, epinephrine produces anxiety and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The compounds of this invention inhibit phenylethanolamine N-methyltransferase and thus reduce the formation of epinephrine. They are therefore useful in situations where there is overproduction of epinephrine or where epinephrine production is detrimental.

The compounds of this invention are represented by the following formula:

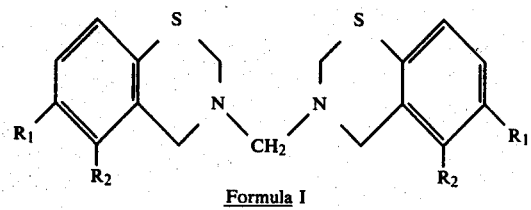

Formula I in which:

$R_1$ is chloro or sulfamoyl; and $R_2$ is chloro or hydrogen.

An advantageous compound of this invention is 3,3'-methylene-bis(2,3-dihydro-6-chloro-4H-1,3-benzothiazine).

The compounds of this invention are prepared by the following procedure:

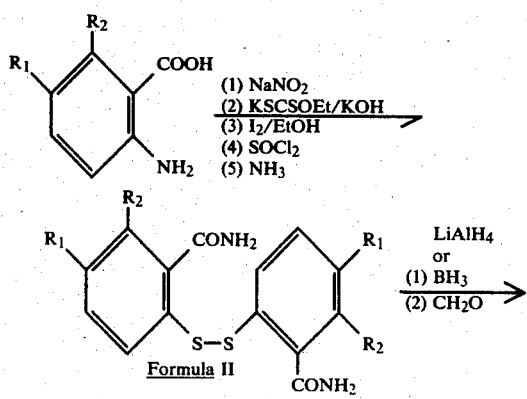

-continued

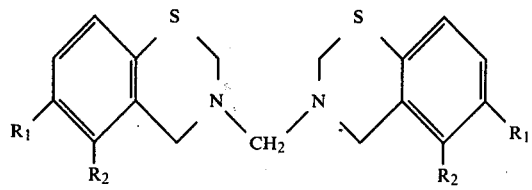

in which $R_1$ and $R_2$ are defined as in formula I.

According to the above procedure, the benzothiazine compounds of this invention are prepared by reducing and cyclizing the appropriately substituted dithiobis benzamide of formula II. The benzamide is reduced with a metallic hydride reagent for example lithium aluminum hydride or diborane. Cyclization is carried out by further treatment with formaldehyde.

The dithiobis benzamide of formula II is prepared by diazotization of the appropriately substituted benzoic acid, conversion of the diazonium salt to the corresponding disulfide followed by amination of the carboxylic acid. The diazotization and amination are carried out by methods well known to the art, for example, diazotization by treatment with sodium nitrite and amination by treatment of the dithiobis benzoic acid with thionyl chloride and ammonia.

The nontoxic pharmaceutically acceptable acid addition salts of the compounds of Formula I as well as the free bases are useful. Such salts are easily prepared by methods known to the art. The free base is treated with an organic or inorganic acid in an aqueous miscible solvent, such as acetone or ethanol. Concentrating and cooling or adding an aqueous immiscible solvent, such as ethyl ether or chloroform, gives the desired salt directly. Exemplary of the salts which are included in this invention are the maleate, fumarate, benzoate, ascorbate, pamoate, succinate, bismethylenesalicylate, methanesulfonate, ethanedisulfonate, benezenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetate, hydrochloride, hydrobromide, sulfate, cyclohexylsulfamate, phosphate and nitrate salts.

The activity of the compounds of formula I is demonstrated by inhibition of phenylethanolamine N-methyltransferase in vitro by the assay procedure described by Pendleton and Snow, *Molecular Pharmacology*, 9:718-725 (1973) at various compound concentrations. For example, at concentrations of $1.0 \times 10^{-4}$ and $1.0 \times 10^{-6}$ M a preferred compound of this invention, 3,3'-methylene-bis(2,3-dihydro-6-chloro-4H-1,3-benzothiazine) as its dihydrochloride salt inhibits phenylethanolamine N-methyltransferase by 99% and 98% respectively.

The pharmaceutical compositions of this invention to inhibit phenylethanolamine N-methyltransferase comprise a pharmaceutical carrier and, as the active ingredient, a benzothiazine compound of formula I. The active ingredient will be present in the compositions of this invention in an effective amount to inhibit phenylethanolamine N-methyltransferase.

Preferably, the compositions of this invention contain the active ingredient of formula I in an amount of from about 50 mg. to about 1000 mg., advantageously from about 100 mg. to about 500 mg., per dosage unit.

The pharmaceutical carrier may be, for example, a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material will known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a bis-benzothiazine compound of formula I.

Preferably, the compounds of formula I are administered in conventional dosage unit forms prepared by combining an appropriate dose of the compound with standard pharmaceutical carriers.

Preferably, the active ingredient of formula I will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of the compounds of this invention and processes for their preparation.

EXAMPLE 1

A solution of 9.4 g. (54.5 MMol) of 2-amino-5-chlorobenzoic acid, 2.3 g. of NaOH (55 MMol) and 3.75 g. (54.5 MMol) of sodium nitrite in 65 ml. of distilled water was added dropwise to a stirred mixture of 15 ml. of concentrated hydrochloric acid and 20 g. of ice. The reaction was stirred in the cold for 20 minutes then neutralized with potassium acetate to pH 5–6. The cooled solution was added in a fine stream to a hot (70°–75°) solution of 25 g. (153 MMol) of potassium xanthate in 80 ml. of water. After addition was complete the reaction was cooled to room temperature and acidified to pH 2 with concentrated hydrochloric acid. The solution was decanted from a gum and the gum dissolved in 80 ml. of 10% sodium hydroxide and heated on a steam bath for two hours. Sodium bisulfite (5.0 g.) was added and the solution heated to 75° for 15 minutes, filtered, cooled and adjusted to pH 3–4 with concentrated hydrochloric acid. The resulting solid was collected and washed with water. It was slurried in 25 ml. of water, 250 ml. of ether was added and the layers separated. The organic phase was dried, filtered and concentrated to give a yellow solid which was dissolved in 400 ml. of ethanol and stirred in an ice-bath while solid iodine was added in small portions until a faint color persisted for thirty minutes. The reaction was concentrated and triturated with 25 ml. of cold methanol to yield 2,2'-dithiobis(5-chlorobenzoic acid) having a melting point of 320°–324° C.

A mixture of 6.09 g. of the above benzoic acid and 15 ml. of thionyl chloride was refluxed until gas evolution ceased. The excess thionyl chloride was stripped off under vacuum and the residue taken up in 30 ml. of toluene and evaporated again. The crude acid chloride was suspended in toluene at about 50° C. and gaseous ammonia was bubbled through. The resulting preceipitate was removed by filtration and crystallized from glacial acetic acid to give 2,2'-dithiobis(5-chlorobenzamide) having a melting point of 278°–282° C.

To a suspension of 2.0 g. (5.2 Mmol.) of 2,2'-dithiobis(5-chlorobenzamide) in 40 ml. of ether was added in portions over thirty minutes 0.8 g. (21 Mmol.) of lithium aluminum hydride. The mixture was refluxed for three hours and then stirred at room temperature overnight. Excess hydride was destroyed by the dropwise addition of 10 ml. of ethyl acetate followed by 50 ml. of 3 N hydrochloric acid. The organic phase was separated, extracted with 25 ml. of 3 N hydrochloric acid and the combined acidic extracts adjusted to pH 5.0 with sodium carbonate. A solution of 5 ml. of 37% formaldehyde was added and the mixture stirred in an ice bath for 15 minutes. The pH was raised to 8.0 with potassium carbonate and the resulting suspension extracted with ethyl acetate. The combined extracts were dried, filtered and evaporated. The residue was dissolved in 20 ml. of ether and treated with 5 ml. of saturated and etheral hydrogen chloride. A gummy solid precipitated which was dissolved and partitioned between 5% sodium bicarbonate and ethyl acetate. The aqueous phase was extracted with ethyl acetate and the combined extracts dried and evaporated. The residue was crystallized from acetone to give as a white solid 3,3'-methylene-bis(2,3-dihydro-6-chloro-4H-1,3-benzothiazine.

The above base was dissolved in 30 ml. of 5:1 ether-/ethyl acetate and treated with 10 ml. of saturated ethereal hydrogen chloride. The resulting precipitate was removed by filtration, washed with ether and dried to give 3,3'-methylene-bis(2,3-dihydro-6-chloro-4H-1,3-benzothiazine) dihydrochloride having a melting point of 231°–236° C.

EXAMPLE 2

Into a solution of 8.2 g. (0.04 Mol.) of 2-amino-5,6-dichlorobenzoic acid in 100 ml. of ether and 5 ml. of methanol is bubbled a twofold excess of diazomethane. The reaction is stirred in the cold for 15 minutes and treated with glacial acetic acid to destroy excess diazomethane. The organic phase is washed with 5% sodium bicarbonate, dried, filtered and evaporated. This residue is dissolved in 50 ml. of ether and treated with ethereal hydrogen chloride. The resulting precipitate is collected, washed with ether and dried to give 8.1 g. of cream colored crystals. Crystallization from isopropanol gave white crystals (melting point 185°–189° C.). A suspension of 1.1 g. (5 Mmol.) of the free base of this amine in 20 ml. of fluoroboric acid was cooled in an ice bath while a solution of 0.35 g. (5 MMol.) of sodium nitrite in 5 ml. of water was added dropwise. The mixture was stirred in the cold for 30 minutes. The precipitate was removed, washed with three 20-ml. portions of ethanol and two 30-ml. portions of ether and dried. It was added carefully in small portions to 1.60 g. of potassium ethyl xanthate in 20 ml. of water at 75°–80° C. After addition was complete, it was stirred at 80° C. for 30 minutes. The reaction was cooled and acidified with hydrochloric acid. It was extracted with three portions of ethyl acetate and the extracts dried, filtered and concentrated. The residue was dissolved in 35 ml. of 95% ethanol containing 5 g. of sodium hydroxide and refluxed. The mixture was diluted with 100 ml. of water, extracted with ether, acidified with concentrated hydrochloric acid and again extracted with ether. The acidic extracts were dried and evaporated. The residue was taken up in 30 ml. of methanol and treated with iodine until a faint color persisted. The mixture was evaporated and the residue crystallized from methylene chloride to give 6,6-dithiobis(2,3-dichlorobenzamide).

Substituting the above dichlorobenzamide for monochloro benzamide and following the procedure of Example 1, 3,3'-methylene-bis(2,3-dihydro-5,6-dichloro-4H-1,3-benzothiazine)dihydrochloride is prepared.

EXAMPLE 3

A solution of 10 g. of 2-carboxy-4-sulfamoylbenzenethiol in 200 ml. of dry methanol is treated with iodine in portions until a pink color persists. The mixture is evaporated and the residue crystallized from methylene chloride to give 2,2'-dithiobis(5-sulfamoylbenzamide).

A solution of 46 g. of 2,2-dithiobis(5-sulfamoylbenzamide) in 50 ml. of tetrahydrofuran is treated dropwise with 40 ml. of 1 molar borane in tetrahydrofuran. The mixture is refluxed for one hour, cooled, treated carefully with 10 ml. of concentrated hydrochloric acid and refluxed again. The tetrahydrofuran is evaporated and the residue partitioned between ethyl acetate and water. The aqueous phase is separated, adjusted to pH 5, and 10 ml. of 37% formaldehyde is added. The mixture is stirred in an ice bath while the pH is raised to 8.5. The suspension is extracted with ethyl acetate which is dried, filtered, and evaporated. The free base is treated with ethereal hydrogen chloride and crystallized to give 3,3'-methylene-bis(2,3-dihydro-6-sulfamoyl-4H-1,3-benzothiazine)dihydrochloride.

EXAMPLE 4

A solution of 18 g. of 3-chloro-2-methylacetanilide in 50 ml. of chlorosulfonic acid is heated for one hour on a steambath, cooled, and poured into ice water to give a solid precipitate. This is removed by filtration, washed with cold water and then treated with 50 ml. of concentrated ammonium hydroxide. The mixture is again heated on a steam bath for one hour, poured into ice water, filtered, and the filtrate washed with water, dried and crystallized to give 4-sulfamoyl-3-chloro-2-methyl acetanilide. A mixture of 15.8 g. of the acetanilide, 18.6 g. of magnesium sulfate, and 26.4 g. of potassium permanganate in 1400 ml. of water is refluxed for twelve hours. Sodium carbonate (26 g.) is added carefully in portions and the solution filtered and acidified to give 4-sulfamoyl-3-chloro-2-carboxyacetanilide which is hydrolyzed by refluxing in a mixture of concentrated hydrochloric acid and ethanol to give 2-amino-5-sulfamoyl-6-chlorobenzoic acid. When this is substituted for 2-amino-5-chlorobenzoic acid in Example 1, the corresponding 6,6'-dithiobis(2-chloro-3-sulfamoylbenzamide) is produced.

Further, by following the procedures set forth in Example 1 and employing the above 2-chloro-3-sulfamoylbenzamide, there is obtained 3,3'-methylene-bis(2,3-dihydro-5-chloro-6-sulfamoyl-4H-1,3-benzothiazine) dihydrochloride.

EXAMPLE 5

| Ingredients | Amounts |
|---|---|
| 3,3'-Methylene-bis(2,3-dihydro-6-chloro-4H-1,3-benzothiazine) dihydrochloride | 200 mg. |
| Calcium sulfate dihydrate | 150 mg. |
| Sucrose | 25 mg. |
| Starch | 15 mg. |
| Talc | 5 mg. |
| Stearic acid | 3 mg. |

The calcium sulfate dihydrate, sucrose, and the benzothiazine are thoroughly mixed and granulated with 10% gelatin solution. The wet granules are screened, dried, and then mixed with starch, talc, and stearic acid, screened and compressed into a tablet.

One tablet is administered three times a day.

EXAMPLE 6

| Ingredients | Amounts |
|---|---|
| 3,3'-methylene-bis(2,3-dihydro-6-sulfamoyl-4H-1,3 benzothiazine) dihydrochloride | 100 mg. |
| Lactose | 400 mg. |

The ingredients are mixed and filled into a hard gelatin capsule.

One capsule is administered three times a day.

What is claimed is:

1. A chemical compound of the formula:

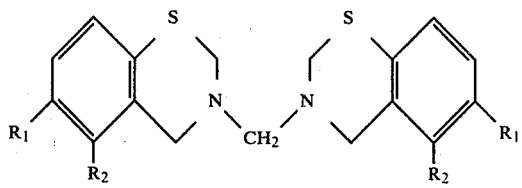

in which:
R₁ is chloro or sulfamoyl; and R₂ is chloro or hydrogen; or a pharmaceutically acceptable acid addition salt thereof.

2. A chemical compound of claim 1 in which R₁ is chloro.

3. A chemical compound of claim 2 in which R₂ is hydrogen.

4. A chemical compound of claim 1 in which R₁ is sulfamoyl.

5. A chemical compound of claim 4 in which R₂ is hydrogen.

6. A chemical compound of claim 3 in which the compound is 3,3'-methylene-bis(2,3-dihydro-6-chloro-4H-1,3-benzothiazine) or a pharmaceutically acceptable acid addition salt thereof.

7. A chemical compound of claim 6 in the form: its dihydrochloride salt.

8. A pharmaceutical composition in dosage unit form for inhibiting phenylethanolamine N-methyltransferase comprising a pharmaceutical carrier and a chemical compound as defined in claim 1.

9. A pharmaceutical composition in dosage unit form for inhibiting phenylethanolamine N-methyltransferase comprising a pharmaceutical carrier and a chemical compound as defined in claim 2.

10. A method of inhibiting phenylethanolamine N-methyltransferase which comprises administering to an animal requiring said inhibition an amount sufficient to produce said inhibition of a chemical compound as defined in claim 1.

11. A method of inhibiting phenylethanolamine N-methyltransferase which comprises administering to an animal requiring said inhibition an amount sufficient to produce said inhibition of a chemical compound as defined in claim 2.

12. A method of inhibiting phenylethanolamine N-methyltransferase which comprises administering to an animal requiring said inhibition a dosage unit containing from about 50 mg. to about 1000 mg. of a chemical compound as defined in claim 1.

* * * * *